United States Patent [19]

Kono et al.

[11] Patent Number: 6,108,607
[45] Date of Patent: Aug. 22, 2000

[54] METHOD OF RATE CALCULATION

[75] Inventors: Toshiaki Kono, Yamaguchi-ken; Hidechika Hayashi; Tetsufumi Matsumoto, both of Kanagawa-ken, all of Japan

[73] Assignee: Tosoh Corporation, Japan

[21] Appl. No.: 08/899,605

[22] Filed: Jul. 24, 1997

[30] Foreign Application Priority Data

Jul. 24, 1996 [JP] Japan .................................. 8-194807

[51] Int. Cl.$^7$ .................................................. C12M 1/34
[52] U.S. Cl. ......................................... 702/22; 435/287.1
[58] Field of Search ................................ 702/22, 23, 24, 702/25, 26; 435/4, 5, 6, 7.1, 8, 9, 10, 11, 12, 287.1

[56] References Cited

U.S. PATENT DOCUMENTS

| | | | |
|---|---|---|---|
| 3,881,992 | 5/1975 | Ralston | 195/103.5 R |
| 4,338,279 | 7/1982 | Orimo et al. | 422/64 |
| 4,657,854 | 4/1987 | Wegfahrt, Jr. | 435/14 |
| 5,500,188 | 3/1996 | Hafeman et al. | 422/82.02 |
| 5,527,710 | 6/1996 | Nacamulli et al. | 436/517 |
| 5,745,385 | 4/1998 | Hinsberg, III et al. | 364/578 |

Primary Examiner—Marc S. Hoff
Assistant Examiner—Craig Steven Miller
Attorney, Agent, or Firm—Nixon & Vanderhye

[57] ABSTRACT

A method of rate calculation in which, in connection with a reaction in which the substrate of an enzyme undergoes the action of the enzyme to be converted to a reaction product, a signal correlated to the concentration of the reaction product is measured at different points of time, those measured values obtained which exceed the upper limit preset in accordance with the detection limit of a detector to be used are excluded while selecting those measured values obtained at different points of time at least equal in number to the independent parameters of the approximating function and which are not greater than said upper limit and the measured values thus selected are weighted by a finite value to effect approximation by said function, provided that said finite value for weighting at least a portion of the measured values are changed continuously in accordance with the magnitudes of said specific measured values. This method is capable of calculating the rate of enzyme activity to accomplish precise quantification of a substance without impairing the continuity of a calibration curve even if measurements are conducted at discontinuous points of time over a measurement range where the rate will change under the influence of the concentrations of the substrate and the reaction product in the reaction mixture.

8 Claims, 7 Drawing Sheets

METHOD OF RATE CALCULATION

BACKGROUND OF THE INVENTION

This invention relates to a method of calculating the rate of increase in the products of enzymatic reactions. More particularly, the invention relates to a method which, in the utilization of enzymatic reactions to quantitate substances as in enzyme immunoassays, is capable of providing continuous calibration curves for overall concentration range while enabling highly precise quantification of a substance of interest in the low-concentration range.

Methods of quantitating substances utilizing enzymatic reactions are currently utilized in many biochemical and immunological tests. For example, the general practice in enzyme immunoassays comprises mixing a specimen such as human serum with an immobilized antibody against an analyte and an enzyme-labelled antibody against the analyte to form an immune complex, causing the enzyme in the complex to react with a substrate, measuring the concentrations of the resulting product of the enzymatic reaction to determine the rate of its increase and comparing the measured values with a calibration curve preliminarily constructed by performing similar procedures on a standard sample containing known concentrations of the analyte.

In practice, the reaction product is not directly measured but signals correlated to its concentration such as the intensity of fluorescence and the absorbance of light are measured.

Problems with the methods of quantitating substances utilizing enzymatic reactions are that when an enzyme is allowed to react with its substrate for a prolonged time, the concentration of the enzyme's substrate decreases and as the concentration of the reaction product increases, the rate of its increase decreases, and that during the reaction the enzyme has the potential to be inactivated over time under the influence of the components in the reaction mixture. Decreases of the similar kinds may also occur depending upon the detection system employed.

Under the circumstances, in most methods of quantitating substances utilizing the rate of increase in the enzymatic reaction products, it is common practice to measure the product of enzymatic reaction within limits (a concentration range) where the measurement is not highly sensitive to the effects of the concentrations of the substrate and the reaction product while ensuring that the time of measurement is restricted within limits where the enzyme will not be inactivated by the components of the reaction mixture. If these conditions are conformed, the concentration of the reaction product vs the point of time of measurement can be approximated by a linear function and the slope of this linear function is the rate of increase in the reaction product, or commonly termed the "rate of enzymatic reaction".

However, the rate of increase in the reaction product which is calculated using the values obtained by measurements within said limits of concentration range and time is sensitive to slight variations of measurement value and conditions and this has been a problem in biochemical and immunonological tests which require good reproducibility and high precision in measurement.

If such restricted conditions are not observed but the range of measurement is expanded to those concentrations of the reaction product at which the concentration of the substrate or the reaction product is influential on the enzyme's activity, the relationship between the time of measurement and the concentration of the reaction product becomes curvilinear and cannot appropriately be approximated by a linear function. If the range of measurement time is increased with a view to reducing the variations in the calculated values of rate, more of the measured values will exceed the upper limit of measurement with the detector from the stage where the enzyme's activity is comparatively low. Therefore, if measurements are conducted at discontinuous points of time and if the obtained values of measurement are approximated by a linear function, with its slope being equated as the rate of increase in the enzymatic reaction product, the rate of increase calculated when the number of effective measurements changes will change in a non-continuous manner and a plot of the rate against enzyme's activity may potentially lose continuity or smoothness (the continuity of differential values).

This phenomenon could be avoided if the measured values obtained by measurement at continuous points of time were approximated by a linear function; however, in the areas of biochemical and immunological tests where large volumes of samples have to be quantitated, there is a need to process many samples and if the detector is occupied for a long period by procedures for a single sample, the processing speed decreases to eventually cause the problem of a failure to meet the aforementioned requirement.

Another problem with the quantitation of substances utilizing enzymes is that since a plurality of measurement systems involve variations in operating parameters such as the amount of a sample to be dispensed, the amount of the reaction mixture, the reaction temperature and the state of agitation of the reaction mixture, it is necessary to perform quantification in collation against the calibration curve obtained with an identical measurement system. This enables consistent measurements over a broad range of concentrations; however, if the measurement is conducted at discontinuous points of time with the result being approximated by a linear function as described above, the continuity and smoothness of the calibration curve is lost rather than maintained and if, in order to solve this problem, measurements are made at continuous points of time, the rapidity in measurement which is required in areas such as biochemical and immunological tests cannot be insured.

SUMMARY OF THE INVENTION

An object of the present invention is to provide a method of calculating the rate of enzyme's activity, in which even if the number of measured values changes over the range of concentrations or time where the rate of increase in the reaction product can vary under the influence of the concentrations of the substrate and the reaction product in the reaction mixture, as well as the enzyme inactivating components, the continuity of and smoothness of the calibration curve and even its linearity will not be impaired but exact quantification of a substance of interest can be accomplished from the obtained measured values.

This object of the invention can be attained by a method of rate calculation which, in connection with a reaction in which the substrate of an enzyme undergoes the action of the enzyme to be converted to a reaction product, measures at different points of time a signal correlated to the concentration of the reaction product, approximates the obtained measured values by a specified function of the time of measurement and determines the slope of said function to establish the rate of increase in said reaction product, wherein those measured values obtained which exceed the upper limit preset in accordance with the detection limit of a detector to be used are excluded while selecting those measured values obtained at different points of time at least equal in number to the independent parameters of the approximating function and which are not greater than said upper limit and wherein the measured values thus selected are weighted by a finite value to effect approximation by said function, provided that said finite value for weighting at least a portion of the measured values being changed continuously in accordance with the magnitudes of said specific measured values.

The same object of the invention can be attained by a method of rate calculation which, in connection with a reaction in which the substrate of an enzyme undergoes the action of the enzyme to be converted to a reaction product, measures at different points of time a signal correlated to the concentration of the reaction product, approximates the obtained measured values by a nonlinear function of the time of measurement and determines the rate of increase in said reaction product from said function, wherein those measured values obtained which exceed the upper limit preset in accordance with the detection limit of a detector to be used are excluded while selecting those measured values obtained at different points of time at least equal in number to the independent parameters of the approximating function and which are not greater than said upper limit and wherein the measured values thus selected are weighted by a finite value to effect approximation by said function and the slope of a tangent line on said function is determined to establish the rate, with the point of time for determining the slope of said tangent line being shifted.

EXPLANATION OF THE SYMBOLS 1. uv lamp
2. interference filter (340–390 nm)
3. dichroic mirror
4. condenser lens
5. test cup
6. substrate solution
7. interference filter (450–480 nm)
8. photodiode
9. cup supporting block
10. aluminum plate
11. stirring magnet plate
12. heater
13. amplifier
14. VF converter
15. counter
16. computer

DETAILED DESCRIPTION OF THE PREFERRED EMBODIMENTS

The present invention will now be described below in detail.

The invention is applicable to any measurement systems as long as they involve enzymatic reactions. Thus, the invention is effective not only in a measurement that utilizes an enzyme as a label to quantify another substance but also in a measurement that performs quantitation of the enzyme itself. Stated more specifically, the invention is applicable to any measurement systems capable of monitoring the state of a reaction, as exemplified by methods including a procedure for measuring the concentration of an enzyme and even that of another substance in terms of signals such as the absorbance of light and the intensity of fluorescence that are correlated to the concentration of the reaction product generated by an enzymatic reaction. In this case, if the substrate itself has the property of emitting light such as fluorescence at a specified wavelength but the enzymatic reaction product does not emit any light such as fluorescence at said wavelength, measurement of that wavelength will produce signals which decrease in correlation to the increasing amount of the reaction product; on the other hand, if the substrate itself has such a property that it will not emit any light such as fluorescence at a specified wavelength but the enzymatic reaction product emits light such as fluorescence at said wavelength, measurement of that wavelength can produce signals which increase in correlation to the increasing amount of the reaction product.

Examples of the enzyme that may be used in the measurements described above include complexes the enzyme forms by binding with other substances used in enzyme immunoassays and the like, as well as partial modifications thereof. Alternatively, the enzyme may be of such a type that part of its inherent portion has been cleaved or digested, with the enzyme activity being retained. An example of the enzymes to be used in enzyme immunoassays is an alkaline phosphatase (ALP) and an example of the substrate therefor is 4-methyl-umbelliferone phosphate (4 MUP). In a specific example, 4 MU is excited with an excitation wavelength of 350–380 nm and fluorescence at 450–480 nm is measured.

The substrate concentration to be used in the performance of enzymatic reaction is preferably such that the enzyme can exhibit Vmax, or a maximum rate of reaction with the substrate, in the early period of reaction, namely, within a comparatively short time after the enzyme contacts the substrate; however, this value of concentration is not the sole case of the invention and nearby values will suffice. The amount of the substrate solution may be determined as appropriate depending on the point of time up to which the measurement is continued after the start of enzymatic reaction. In addition, particularly where the enzyme is immobilized either directly or indirectly via an antigen or antibody as in the case of using an insoluble carrier as in enzyme immunoassays, the entire portion of the reaction mixture is preferably agitated to eliminate any density gradient of the substrate.

In accordance with the invention, the measured values finally obtained are approximated by a specified function with respect to the times of measurement at which those values were obtained and, thereafter, the slope of the function is determined to calculate the rate of increase in the concentration of the enzymatic reaction product. The first requirement of this invention is to provide measured values that were obtained by measurements at different points of time no fewer than the independent parameters of the function by which said values are to be approximated. Secondly, of these measured values obtained by measurement at different points of time, those values which are at least equal in number to the parameters of the approximating function must fall within a range not exceeding the upper limit which is set in accordance with the detection limit of the detector used in the measurement. Obviously, the measured values exceeding the upper limit should not be used in rate calculation in view of the physical detection limit of the detector. Since the lower limit of detection is not usually a significant problem, practical purposes can be served if the measured values at least equal in number to the independent parameters of the approximating function fall within a range not exceeding the upper limit which is set in accordance with the detection limit of the detector used in the measurement. Before the measurement, it is not known whether the measured values will exceed said upper limit, so in the usual case, measurements are conducted at different points of time exceeding the number of said parameters so as to obtain more measured values than said parameters and those measured values which do not exceed said upper limit may be selected from the measured values thus obtained. It should be noted that the independent parameters as referred to in the invention do not include known parameters.

Th Suppose that the approximating function is a linear equation expressed by ax+b. Since the equation contains two parameters, a and b, it is required to provide measured values by performing measurements at two or more different points of time and it is also required that at least two of these measured values should not exceed the upper limit which is set in accordance with the detection limit of the detector used. If the approximating function is a quadratic equation expressed by $ax^2+bx+c$ or a linear fractional equation expressed by $1/(y+c)=a/x+b$, three parameters are involved, a, b and c. Hence, it is required to provide measured values by performing measurement at three or more different points of time and it is also required that at least of three measured these values should not exceed the upper limit which is preset in accordance with the detection limit of the detector. Of course, there is no upper limit for the number of measurements that are to be conducted at different points of time; however, since the approximation is in most cases performed by a quadratic or cubic equation, the performance of measurements at 4 or 5 points of time may be given as a preferred case.

If the measured values obtained by measurements at certain points of time exceed the upper limit which is preset in accordance with the detection limit of the detector used, such values are weighted by zero as will be described later in this specification. This means that those measured values which exceed the upper limit are not used for rate calculation.

The time for measuring a signal derived from the enzymatic reaction product at a certain point of time from the start of the enzymatic reaction may be such that a stable value can be obtained in consideration of relevant factors such as the noise level of the detector used. For example, an integral value of the signals for several seconds around a certain point of time may be substituted for the value of measurement at said certain point of time. The range of measurement for the enzymatic reaction may be such a concentration range that the rate of increase of the reaction product is influenced by a decreasing substrate concentration or an increasing concentration of the reaction product. In other words, the values of measurements which suffice for the present invention are ones at those points of time where the concentration of the reaction product is understood to lie within the above-mentioned range on the basis of measured signals. Alternatively, the present invention permits the values of measurement at points of time within such a time range that the enzyme activity will deteriorate during the reaction under the influence of components of the reaction mixture. Thus, in the present invention, any points of time may be selected for obtaining measured values; however, in identical or similar measurement systems including the detector, a series of measurements are desirably conducted at fixed points of time, particularly in the case where rate calculations are performed with emphasis being placed on reproducibility for the same enzyme and the like.

The weighting of the measured values obtained in the present invention and the exclusion of those measured values which exceed the above-defined upper limit are effective in maintaining the continuity of a calibration curve constructed using an enzyme at known concentrations. This is because the decrease in the number of measurements which is necessitated when the measured value at a certain point of time is anticipated to exceed the above-defined upper limit has the potential to cause a sudden change in the shape of the time-rate plot which is determined from the points of time of measurement and the rate values from the measured values. To avoid this possibility, those values of measurement at points of time which will obviously exceed the above-defined upper limit are weighted by zero (excluded) whereas those values of measurement at points of time which do not exceed the upper limit are weighted by an appropriate finite value.

In the present invention, the weighting of measured values by a finite value so as to perform approximation by a suitable function is characterized in that for at least part of the measured values, said finite weighting value is varied continuously in accordance with said measured values. The number of measured values for which the finite weighting value is varied continuously need not be one and may be two or more. Take, for example, the case where the signal correlated to the product of enzymatic reaction increases with time; since those measured values which exceed the upper limit preset in accordance with the detection limit of the detector are weighted by zero (excluded), the finite value for weighting those measured values which are close to the thus set upper limit (which is hereunder sometimes referred to simply as the "upper limit") is preferably changed to approach zero. The measured values for which the finite weighting value is to be varied continuously are particularly those which are close to the above-defined upper limit. In a system where the increase in the concentration of the reaction product is accompanied by the increase in the intensity (amount) of the signal correlated to said concentration, yn usually increases with the point of time tn and, hence, the measured value obtained at the highest point of time tn of those measured values which satisfy the above-mentioned condition is preferably weighted by a varying value. It should, however, be remembered that the number of measured values to be weighted variably is not limited to one. In another exemplary case, measured values may be weighted by a varying value in inverse correlation to their magnitude.

According to another feature of the invention which will be described later, the continuity and the like of the calibration curve can be insured without varying the finite weighting value. Stated briefly, if the approximating function is an appropriate nonlinear function, those measured values which are equal to or less than the above-defined upper limit are weighted by an invariable finite value for approximation by said function and the slope of said function is determined in terms of the slope of a tangent line on said function, which in turn is substituted as the rate; according to the second feature of the invention, the point of time at which the slope of a tangent line on said function is determined is shifted.

One case of weighting the measured values by the present invention is such that four measured values (t1, y1), (t2, y2), (t3, y3) and (t4, y4) as obtained by measurement at four different points of time (where t desinates a point of time and y a measured value, with $t1 < t2 < t3 < t4$, and y3 in no case exceeds a preset upper limit) are weighted by w1, w2, w3 and w4, and the following settings may be given as examples of the case. In this specification, the values of actual measurement at points of time tn are hereunder designated by yn, etc. and the values of theoretical measurement at certain points of time tx by yx, etc.

(1) When y4 is greater than ymax which is the upper limit set in accordance with the detection limit of the detector used and if y3 is not greater than the upper limit ymax, then w1=w2=w3=1 and w4=0.

(2) If y4 is equal to or smaller than ymax which is the upper limit set in accordance with the detection limit of the detector used, then w1=w2=w3=1 and in addition, w4= $((ymax-y4)/ymax))^n$. In the last equation, n represents a positive number and its value may be determined in consideration of the point of time and the like. Usually, a positive number in the range of 1–20 is selected as n. Further, as will be described later, if the point of time at which the slope of a tangent line is to be shifted, then w1=w2=w3=w4=1 is acceptable.

In the case (1), the weight is exemplified by w1=w2=w3=1 and in the case (2) by w1=w2=w3=1 (or w1=w2=w3=w4=1). If it is anticipated that the measured value y1 at the point of time t1 is likely to fluctuate due, for example, to instability in temperature, a suitable adjustment may be made by, for example, changing the value of w1 to 0.5. If the finite value for weighting is to be varied in the case (2), the value of w4 may be set as follows.

(3) In the case (2), w4=1 if y4<ymax/2 or w4=$(2\times(ymax-y_4)/ymax)^n$ if $ymax/2 \leq y4 \leq ymax$.

If the present invention is to be applied to an enzyme immunoassay, particularly, to the measurement of enzyme activity which is correlated to the concentration of an analyte in the sample, the performance of four or so measurements as already mentioned hereinabove may be given as a preferred example; however, in order to determine whether the finite value for weighting the measured values obtained should be varied or fixed in the case just described above, the actual measurement system, particularly, the points of time at which the measurement is conducted are preferably taken into consideration. For example, if the point of time for measurement tn is sufficiently shorter (smaller) than the time required for the analyte to reach a concentration at which the enzyme activity is influenced by the substrate concentration which decreases with the progress of the enzymatic reaction or by the increasing concentration of the reaction product that it is impossible for the yn measured at said point of time to exceed the above-defined upper limit, there is no need to vary the finite weighting value. Conversely, if the point of time for measurement tn is equal to or near the time required for the analyte to reach the concentration at which the enzyme activity is influenced by the substrate concentration which decreases with the progress of the enzymatic reaction or by the increasing concentration of the reaction product, the finite weighting value is advantageously varied unless the yn measured at said point of time exceeds the above-defined upper limit (the weight is zero if the upper limit is exceeded). To give a more specific example, suppose the case where the points of time t1, t2, t3 and t4 are 20 seconds, 50 seconds, 80 seconds and 290 seconds, respectively, such that t4 or the point of time for the last measurement is as long as 290 seconds from the start of the enzymatic reaction which is close to the time required for the analyte to reach the concentration at which the enzyme activity is influenced by the decreasing substrate concentration or the increasing concentration of the reaction product but t3 or the point of time for the third measurement is sufficiently shorter (smaller) than that time; in this case, the weight for y4 is reduced to zero if it is greater than the upper limit whereas y1–y3 are weighted by a fixed finite value; on the other hand, if y4 does not exceed the upper limit, it is preferred that y1–y3 are weighted by a fixed finite value whereas y4 is weighted by a finite variable value.

Another case of weighting the measured values by the present invention is such that five measured values (t1, y1), (t2, y2), (t3, y3), (t4, y4) and (t5, y5), as obtained by measurements at five different points of time (where t designates a point of time and y a measured value, with $t1<t2<t3<t4<t5$, and y3 in no case exceeds a preset upper limit) are weighted by w1, w2, w3, w4 and w5, and the following settings may be given as examples of the case.

(4) When y4 is greater than ymax which is the upper limit set in accordance with the detection limit of the detector used and if y3 is not greater than the upper limit ymax, then w1=w2=w3=1 and W4=w5=0.

(5) If only y5 is greater than ymax which is the upper limit set in accordance with the detection limit of the detector used, then w1=w2=w3=1 and W5=0 and, in addition, W4=$((ymax-y4) \times t5/(ymax \times (t5-t4)))^n$.

(6) If y5 is equal to or smaller than ymax which is the upper limit set in accordance with the detection limit of the detector used, then w1=w2=w3=w4=1 and, in addition, w5=$((ymax-y5)/ymax)^n$ In the cases (4)–(6), too, if it is anticipated that the measured value y1 at the point of time t1 is likely to fluctuate, a suitable adjustment may be made by, for example, changing the value of w1 to 0.5. In addition, as in the above case (2), wx (the value of w4 or w5) may be equal to 1 if yx<ymax/2; alternatively, if ymax/2≦yx≦ymax, w4 may be equal to $(2\times(ymax-y3)\times t5/(ymax\times(t5-t4)))^n$ and w5 to $(2\times(ymax-y4)/ymax)^n \times x=4$ or 5).

As in the previous case, in order to determine whether the finite value for weighting the measured values obtained should be varied or fixed in the above-described case of performing measurement at five different points of time, the actual measurement system, particularly, the points of time at which the measurement is conducted are preferably taken into consideration.

If the point of time at which a measured value is obtained is written as x and the concentration of the enzymatic reaction product as y, preferred examples of the function by which the measured values can be approximated may include a linear function expressed by $y=ax+b$, a quadratic function expressed by $y=ax^2+bx+c$ and a linear fractional equation expressed by $y=(ax+b)/(x+c)$; there are no particular limitations on the approximating function that can be used as long as it is an increasing function of x.

In the case where the measured values are approximated by a nonlinear function through the application of the method of least squares or the like, the slope of that function can generally be determined as the slope of a tangent line at a given point on the graph representing that function. Depending on the upper limit which is set in accordance with the detection limit of the detector used, not all of the measured values are used in the rate calculating method of the invention but the number of measured values to be used in the calculation is occasionally smaller than the number of actual measurements, as exemplified by the case where the measured values that exceed said upper limit are weighted by zero and not used in the subsequent steps of rate calculation. However, in the present invention, the calculation is performed in such a way that the point of time at which the slope of a tangent line on the curve of the approximating function is optionally shifted to a point of time where the least effect is caused by the variation in values measured or the decrease in the number of measurements, thereby giving only those measured values which do not exceed the above-defined upper limit, and this is effective in excluding the adverse effect of the decrease in the number of measured values. An optimal method of shifting the point of time for determining the slope of the tangent line(i.e., the rate of increase in the enzymatic reaction product) can be selected in consideration of such factors as the type of enzyme to be assayed and the upper limit which is set in accordance with the detection limit of the detector used for measurement.

For example, in the case where the points of time for measurement fall within the range of time during which the deactivation of the enzyme due to the components of the reaction mixture is sure to occur, the rate determining point of time does not have to be shifted but may be shifted and is preferably fixed. Consider, for example, four measured values (t1, y1), (t2, y2), (t3, y3) and (t4, y4) as obtained by measurement at four different points of time (where t designates a point of time, y a measured value, and t1<t2<t3<t4); in this case, the rate determining point of time (tx, which is not limited to those points of time where the actual measurement was conducted) is selected at a fixed point of time that exists between t1 and t4.

If y4, which is the value of measurement at t4, is likely to exceed the upper limit which is set in accordance with the detection limit of the detector used in the measurement, tx is preferably selected at a point of time tx which exists between the average of t1, t2 and t3 and that of t1, t2, t3 and t4. Assume that the points of time for measurement are 30, 60, 120 and 240 seconds, respectively, from the start of the enzymatic reaction; in this case, the rate is preferably determined with tx being selected at a point of time that exists between the average of t1, t2 and t3 in the illustrated case (which is 70 seconds) and the average of t1, t2, t3 and t4 (which is 112.5 seconds), namely, between 70 and 112.5 seconds.

On the other hand, if the points of time for measurement do not fall within the range of time during which the deactivation of the enzyme will occur due to the components of the reaction mixture, the rate determining point of time is preferably shifted to a point of time where less effect is caused by the variation in the measured values or the decrease in the number of measurements, thereby giving only those measured values which do not exceed the above-defined upper limit. Consider again four measured values (t1, y1), (t2, y2), (t3, y3) and (t4, y4) as obtained by measurement at four different points of time (where t designates a point of time, y a measured value, and t1<t2<t3<t4); in this case, the rate determining point of time (tx, which is not limited to those points of time where the actual measurement was conducted) is preferably selected at the weighted average of t1, t2, t3 and t4. Stated more specifically, if the respective weights w1, w2, w3 and w4 are adjusted to be such that w1=w2=w3=1 whereas w4 is variable as mentioned in the above case (1) of weighting the measured values, tx may be equal to $(t1+t2+t3+w4\times t4)/(3+w4)$. In this equation, tx is fixed at the average of t1, t2 and t3 if y4 exceeds the upper limit set in accordance with the detection limit of the detector used for the measurement and when w4 or the weight of y4 is zero.

In another shifting method, the rate determining point of time may be shifted particularly in such a way as to enhance the accuracy of quantification in the low concentration region of the reaction product while maintaining the linearity of the calibration curve in a measurement system that involves a certain extent of enzyme deactivation but below the upper limit set in accordance with the detection limit of the detector used for the measurement. Consider, for example, the case where n measured values obtained by measurement at n different points of time are written as (t1, y1),(t2, y2), . . . (tn, yn), with the weight for the value of measurement at point of time tn is written as wn; in this case, two different points of time ta and tb (ta<tb) which exist between t1 and t2 are specified and the rate determining point of time tx may be equated by ta+(tb−ta) x wn.

For the same purpose as described above, the rate determining point of time may be varied with reference to a provisional rate calculated on the basis of part of the measured values. For example, measured values (tp, yp) and (tq, yq), are selected that have been obtained by measurement at least two different points of time (tp<tq) and using a provisional rate S $(=(yq-yp)/(tq-tp))$ calculated from these two measured values and an independently defined reference rate M, the rate determining point of time tx is shifted with reference to the magnitude of S/M. Here, the independently defined reference rate M is a reference for fixing the rate determining point of time when said provisional rate S is equal to or grater than M. Consider again the case where the points of time for measurement are (t1, y1),(t2, y2), . . . (tn, yn), with ta and tb (ta<tb) being specified as two different points of time that exist between t1 and tn; in this exemplary case, if S<M, the rate determining point of time tx may be equated as tx=tb−(tb−ta)×(S/M) and if S≧M, tx may be equated to ta.

In other examples of the invention, the shift of the rate determining point of time tx may be defined as a quadratic function of the above-defined S/M or as higher-degree equations of S/M. Thus, in the above-described case, if S<M, tx may be equated as $tx=tb-(tb-ta)\times(S/M)^2$ and if $S\geq M$, tx may be defined as the function tx=ta. In further examples, if S<M, tx may be equated as $tx=tb-(tb-ta)\times k(k+1)\times(S/M)\times(1-(1/k)\times\cos(S/M\times\pi))$ and if $S\geq M$, tx may be defined as the function tx=ta (Where k is a constant which is equal to or grater than one).

In a particular case of the invention where the rate is determined from the approximating function at point of time tx, if the enzyme activity is anticipated to have decreased at said point of time tx under the influence of the substrate concentration and the reaction product, the rate at issue may be corrected in accordance with the value of measurement yx at said rate determining point of time tx so that the (corrected) rate which would be established if the rate of enzymatic reaction at tx were close to Vmax can be determined by calculation. For example, if the rate at point of time tx is written as R, the corrected rate may be equated by $R\times(1+yx\times\alpha)$ (where $\alpha$ is a correction coefficient).

In the early stage where not much time has passed since the start of enzymatic reaction, the substrate concentration is sufficient and the reaction product which will affect the enzyme activity is present in only a small amount; therefore, the rate of enzymatic reaction is usually close to Vmax. In a case like this, the corrected rate may be equated by $R\times(1+R\times\beta)$ (where $\beta$ is a correction coefficient).

The above-mentioned correction coefficients $\alpha$ and $\beta$ are affected by various factors such as the types and concentrations of the enzyme to be assayed an the substrate used and even the volume of the reaction mixture in which the enzymatic reaction is to be performed and, therefore, those co-efficients are preferably determined as empirical values.

EXAMPLES

The following examples are provided for further illustrating the present invention but are in no way to be taken as limiting.

Example 1

Figure 1:
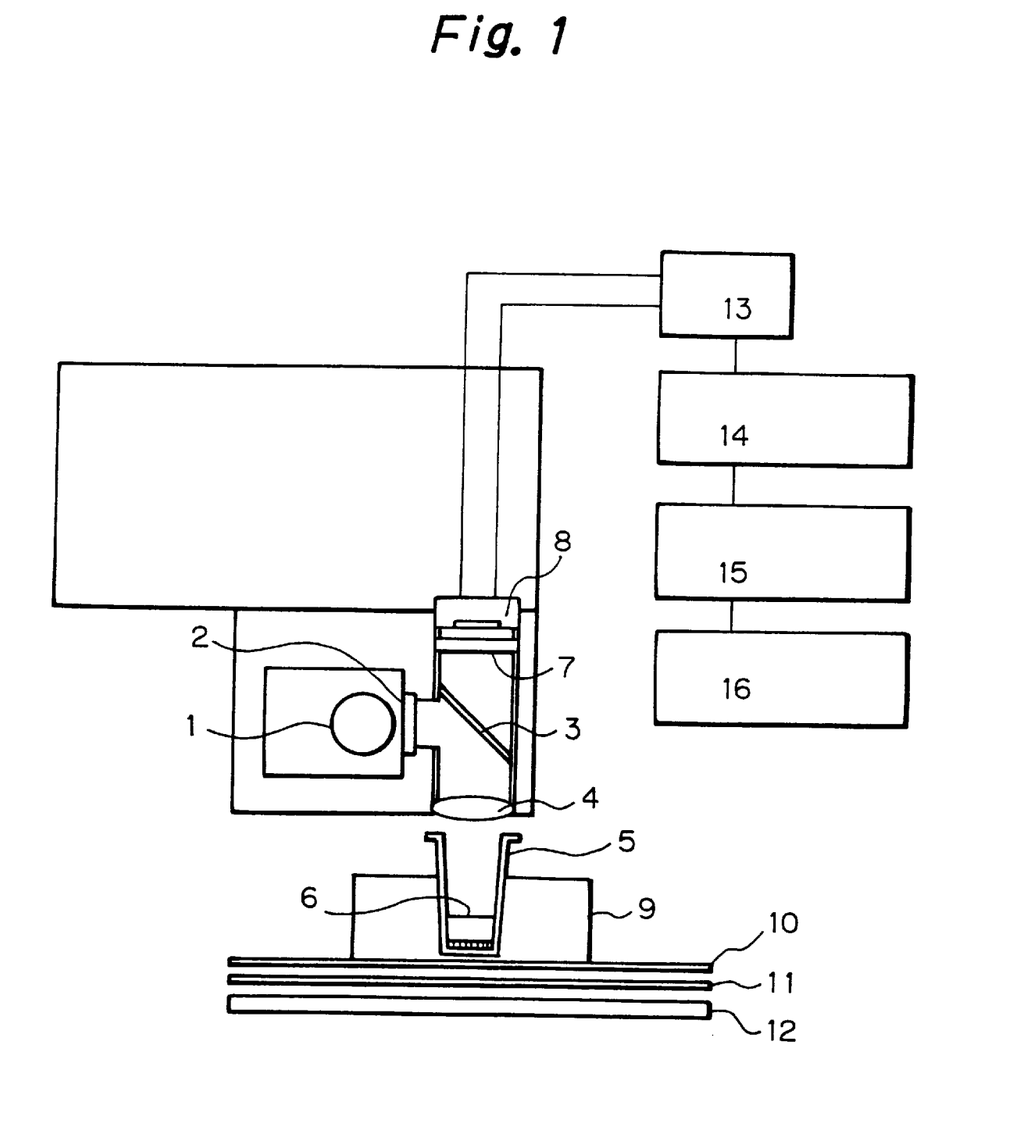
FIG. 1 is a diagram showing a fluorescence detector unit.

A prostate specific antigen (hereunder designated as PA) was quantitated utilizing enzyme activity. A commercial reagent for enzyme immunoassay AIA-PACK PA, a reagent for immunereaction produced by Tosoh Corp.) and a full automatic immunoassay apparatus of the same company (AIA1200) were used. The fluorescenece detector in the analyzer was set up as shown in FIG. 1. The reagent series used comprised as essential components a container of two monoclonal antibodies, one being an anti-PA monoclonal antibody immobilized to beads containing a paramagnetic substance, and the other being a different anti-PA monoclonal antibody to which an alkaline phosphatase (ALP) was bound as a label, and a substrate solution containing an ALP substrate 4-methyl-umbelliferone phosphate (4 MUP).

The fluorescence detector (see FIG. 1) used in Example 1 was composed of a light source 1, an interference filter 2 having a transmission range of 340–390 nm, a dichroic mirror 3 having a reflection band of 350–380 nm and a transmission zone of 420–630 nm, a lens 4 for condensing the light from the source and the fluorescence emitted by 4-methylumbellipherone (4 MU) which is a phosphor occurring as the result of decomposition of 4 MUP by ALP, an interference filter 7 having a transmission range of 450–480 nm, a photodiode 8 for sensing the fluorescence of 4 MU, an amplifier 13 for amplifying signals from the photodiode, a VF converter 14 for digitizing the amplified signals, a counter 15 for cumulatively counting the digitized signals at 0.6-sec intervals, and a computer 16 for storing the cumulative count obtained by counting at 0.6-sec intervals.

In the analyzer used, a reaction vessel 5 into which a substrate 6 was dispensed was supported on an aluminum block 9 resting on an aluminum plate 10. The analyzer also had an agitating mechanism 11 and a temperature control mechanism 12; the agitating mechanism 11 would exert magnetism on the paramagnetic substance in the carrier in the reaction vessel, whereby said carrier would be put into motion to agitate the reaction mixture in the vessel, and the temperature control mechanism 12 would hold the reaction mixture in the vessel at room temperature.

The vessel was charged with 120 $\mu$L of a sample containing PA at a known concentration (0, 14, 28, 57, 115 or 173 g/mL); the PA in each sample was reacted with the two kinds of monoclonal antibody for 40 min to form an immune complex consisting of the PA sandwiched between the carrier=antibody and the antibody=ALP. Then, the liquid component containing the ALP bound antibody which did not form an immune complex was removed from the reaction vessel and washing was performed by repeating the steps of dispensing a liquid detergent and removing the liquid component again. Subsequently, 220 $\mu$L of a substrate solution containing 1 mM of 4 MUP was dispensed and the intensity of fluorescence of 4 MU occurring as the result of decomposition of 4 MUP by ALP was measured continuously for 18–300 seconds after the dispensing of the substrate; the measured fluorescence intensity was converted to the concentration of 4 MU and the rate of 4 MU generation, namely, the rate of increase of the reaction product was calculated from the change (the increase in the case under discussion) in the concentration of 4 MU. This procedure was performed 10 times for each of the samples of the respective PA concentrations. A calibration curve to be used in calculation for converting the measured fluorescence intensity to the concentration of 4 MU was constructed by the following procedure: a 4 MU free solution and a solution containing 10,000 nM of 4 MU were respectively dispensed in an amount of 220 $\mu$L into the same vessel as used in the measurement and the individual fluorescence intensity data (i.e., the data obtained by cumulative counting at 0.6-sec intervals) were correlated with the fluorescence intensities measured at two concentrations of 4 MU (0 and 10,000 nM) to determine a linear function, which was then used as the calibration curve.

Figure 2:
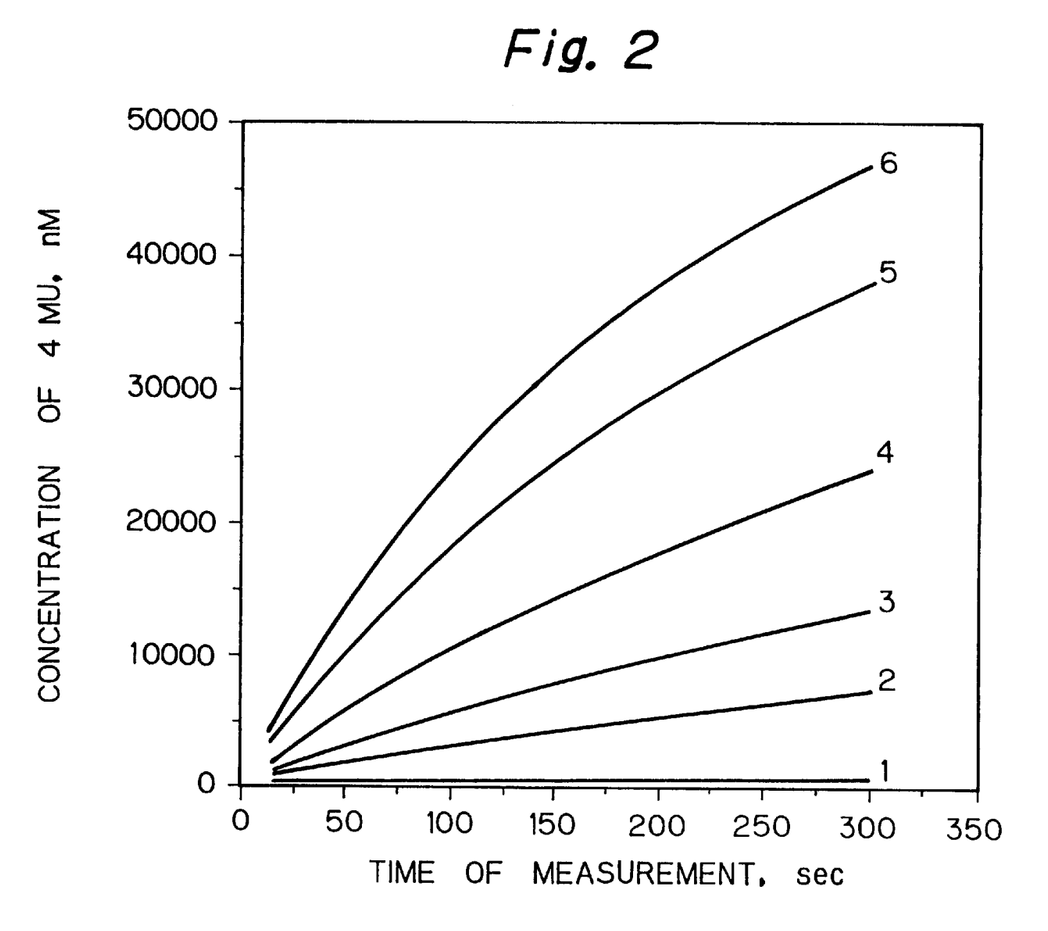
FIG. 2 is a graph showing the results of measurements conducted on samples containing known concentrations of PA in accordance with Example 1 (to investigate the change with time of the concentration of the reaction product (4 MU)); the zero point of measurement time was when the substrate was dispensed; the respective curves in FIG. 2 refer to the results for 0 ng/mL (NO. 1), 14 ng/mL (No. 2), 28 ng/mL (No. 3), 57 ng/mL (No. 4), 115 ng/mL (No. 5) and 117 ng/mL (No. 6).

FIG. 2 is a graph showing the changes in the concentration of 4 MU that occurred during the period of 18–300 seconds after the dispensing of the substrate. Curves 1–6 represent the results for the samples containing PA at respective concentrations of 0, 14, 28, 57, 115 and 173 ng/mL. Obviously, the concentration of 4 MU increased with time but the rate, or the speed of 4 MU production, decreased with the increasing concentration of MU. The apparent decrease in the rate which is evident from FIG. 2 is due not only to the decrease in enzyme's activity that is caused by the decrease in the concentration of the substrate and the increase in the concentration of the decomposition product of the substrate but also to the absorption of excitation light by 4 MU which is the decomposition product of the substrate.

Figure 3:
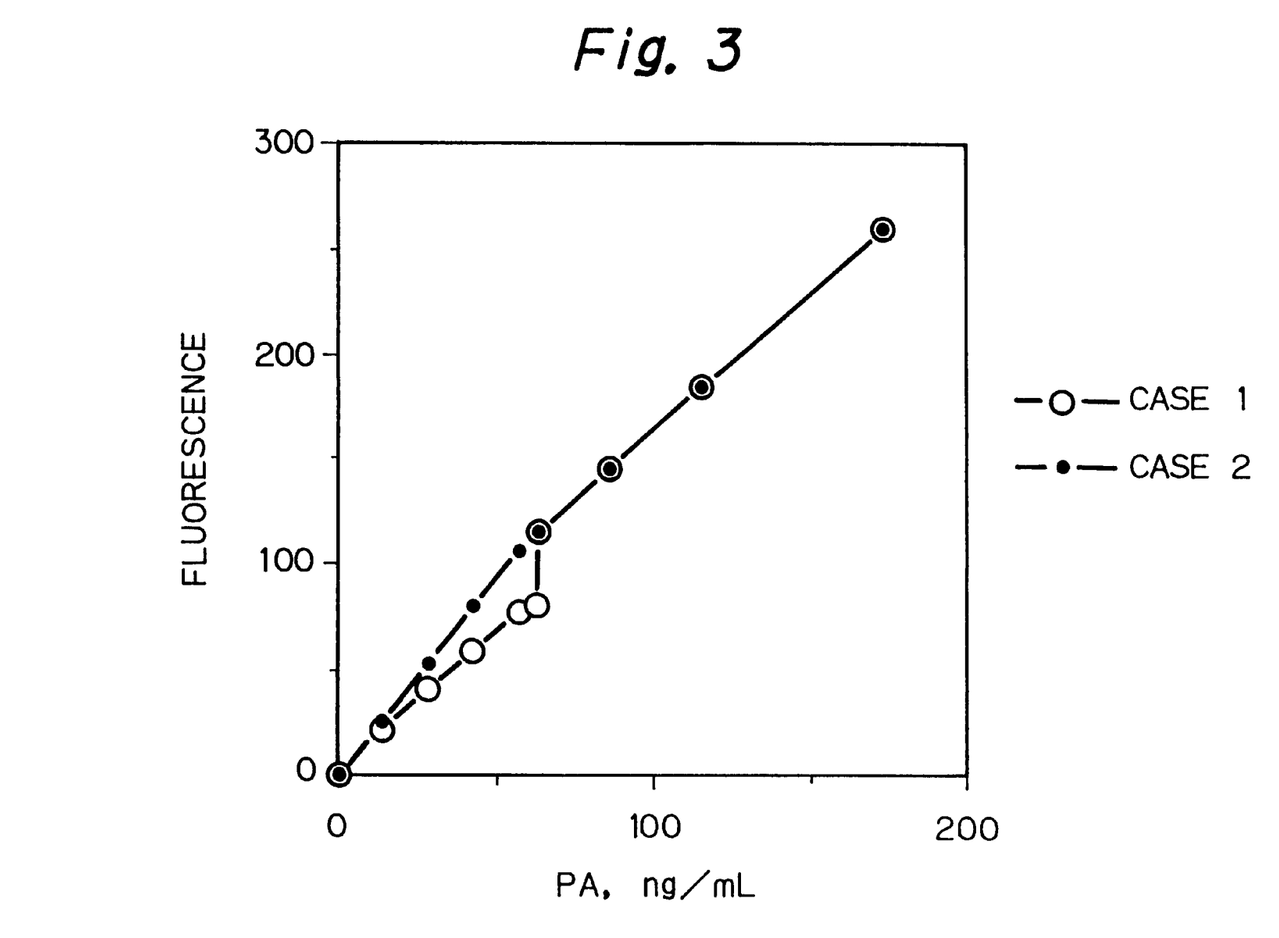
FIG. 3 is a graph comprising the rate at varying concentrations of PA on calibration curves for two cases of weighting three measured values as selected from the results shown in FIG. 2, case 1 (○) being such that the third measured value was weighted by zero when it exceeded the upper limit and by unity when it was not greater than the upper limit and case 2 (●) being such that the third measured value was weighted by zero when it exceeded the upper limit but when it was not greater than the upper limit, the weight was changed in accordance with the method of the invention.

With the 4 MU concentration of 25,000 nM being set as the upper limit, the cumulative values for the following 3-second periods, 18–21 seconds, 48–51 seconds and 288–291 seconds, were selected as single measured values from the data of continuous measurement and rate calculations were conducted on those three cumulative values. When the third measured value was equal to or smaller than the upper limit, it was weighted by one; when it was greater than the upper limit, it was weighted by zero (case 1). In the second case, the method of the present invention was adopted; when the third measured value was equal to or smaller than the upper limit, it was weighted by ((25,000−third measured valued)/25,000)$^{14}$ and when it was greater than the upper limit, it was weighted by zero (case 2). For both cases, the three measured values were approximated by a linear function and its slope was used as the rate; the results are shown in FIG. 3. In order to clarify the positions of discontinuous points, concentrations having no experimental data (e.g. 42 ng/mL, 61.8 ng/mL and 62.8 ng/mL) were determined by interpolation of the 4 MU concentration and utilized in rate calculation. It can be seen that by changing the weight for the measured values at three points of time that were not greater than the upper limit, a generally continuous calibration curve was obtained.

Figure 4:
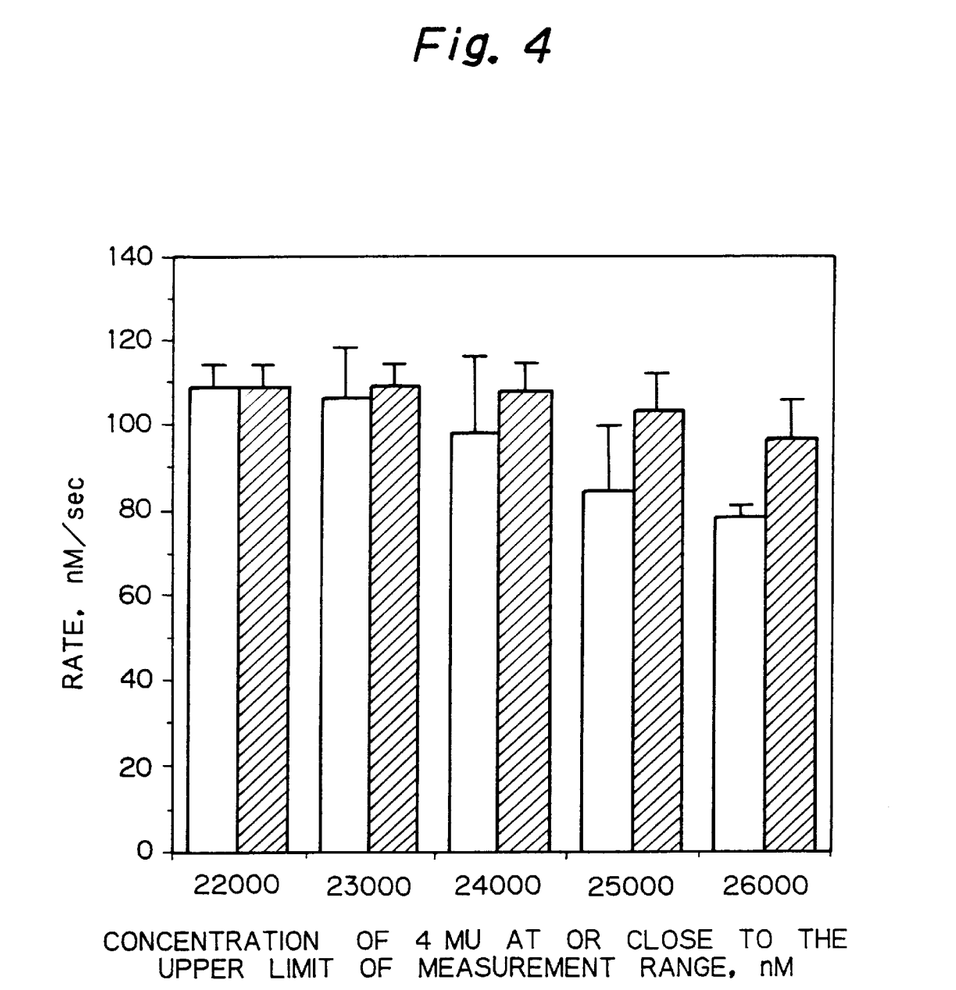
FIG. 4 is a graph showing the result of simulation of rates corresponding to a PA concentration of 57 ng/mL when the upper limit was changed from 22,000 nM to 26,000 nM in terms of 4 MU concentration, in which the clear bars represent case 1, the hatched bars case 2, and the error bars the standard deviations of the rate.

FIG. 4. shows the result of rate calculation by simulating the process by which the third measured value exceeded the upper limit for the case where the PA concentration was 57 ng/mL; the simulation was effected by shifting the upper limit incrementally and the average of 10 rates as well as the change in their standard deviation were compared between case 1 and case 2. In case 1 (clear bars), the rates calculated when the third measured value exceeded the upper limit changed so greatly that it is anticipated that a significant step would occur in the calibration curve. In contrast, in case 2 (hatched bars) where the third measured value not exceeding the upper limit was weighted by a varied value in accordance with the method of the invention, there were no such steps as would occur in case 1 and the variation of measurements was also small; hence, it is anticipated that no steps would occur in the calibration curve. Thus, according to the method of the invention, one can eliminate the possibility of discontinuity (occurrence of steps) in the calibration curve which would otherwise develop if part of the measured values exceeded the upper limit preset in accordance with the detection limit of the detector and were subsequently excluded as being inappropriate for use as data in constructing the calibration curve.

EXAMPLE 2

With the 4 MU concentration of 25,000 nM being set as the upper limit for the measured values obtained in Example 1, the cumulative values for the following 3–second periods, 18–21 seconds 48–51 seconds, 78–81 seconds and 288–291 seconds, were selected as single measured values and rate calculations were conducted on those four cumulative values.

With the fourth measured value being weighted by w4=((25,000−fourth measured value)/25,000)$^2$, the relationship between the point of time and the value of measurement was approximated by a quadratic function using the method of least squares and comparison was made between the following three cases of tx, or the point of time for determining the rate (i.e., the slope of a tangent line on the functional curve): (1) tx=(t1+t2+t3)/3=(19.5+49.5+79.5)/3=49.5 (point of time written as tx1): (2) tx=(t1+t2+t3+t4)/4=(19.5+49.5+79.5+289.5)/4=109.5 (point of time written as tx2); and (3) tx=(t1+t2+t3+t4×w4)/(3+w4) (point of time written as tx3).

Figure 5:
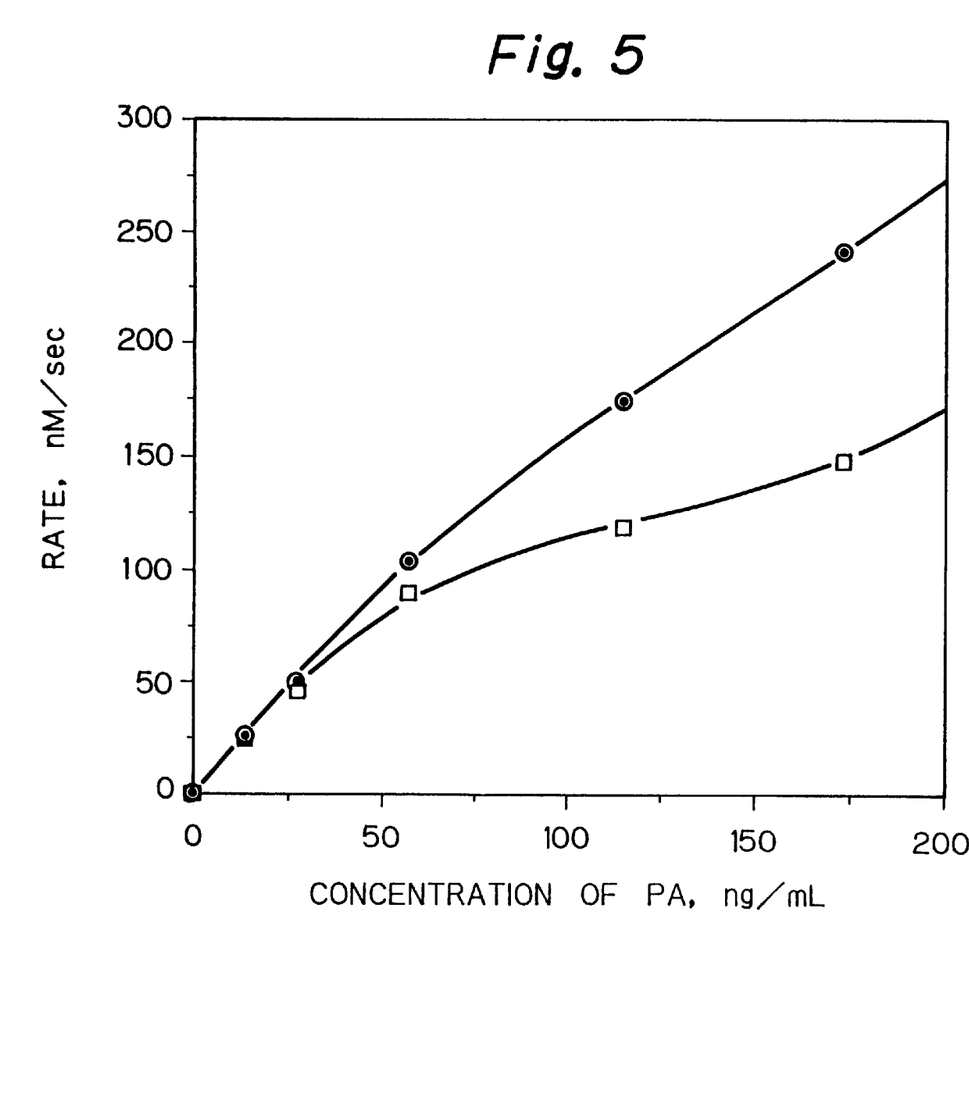
FIG. 5 is a graph showing PA calibration curves for three cases of weighting four measured values, with the relationship between the point of time and the value of measurement being approximated by a quadratic function, the first case (○) being such that tx which was the rate determining point of time was equated by $tx1=(t1+t2+t3)/3$, the second case (□) being such that tx was equated by $tx2=(t1+t2+t3+t4)/4$, and the third case (●) being such that tx was equated by $tx3=(t1+t2+t3+t4\times w4)/(3+w4)$.

FIG. 5 shows PA calibration curves constructed on the basis of the rates determined from the respective points of time tx1, tx2 and tx3. Obviously, the calibration curve derived from the point of time tx3 was in substantial agreement with the calibration curve derived from the point of time tx1 and had a higher degree of linearity than the shape of the calibration curve derived from the point of time tx2.

Figure 6:
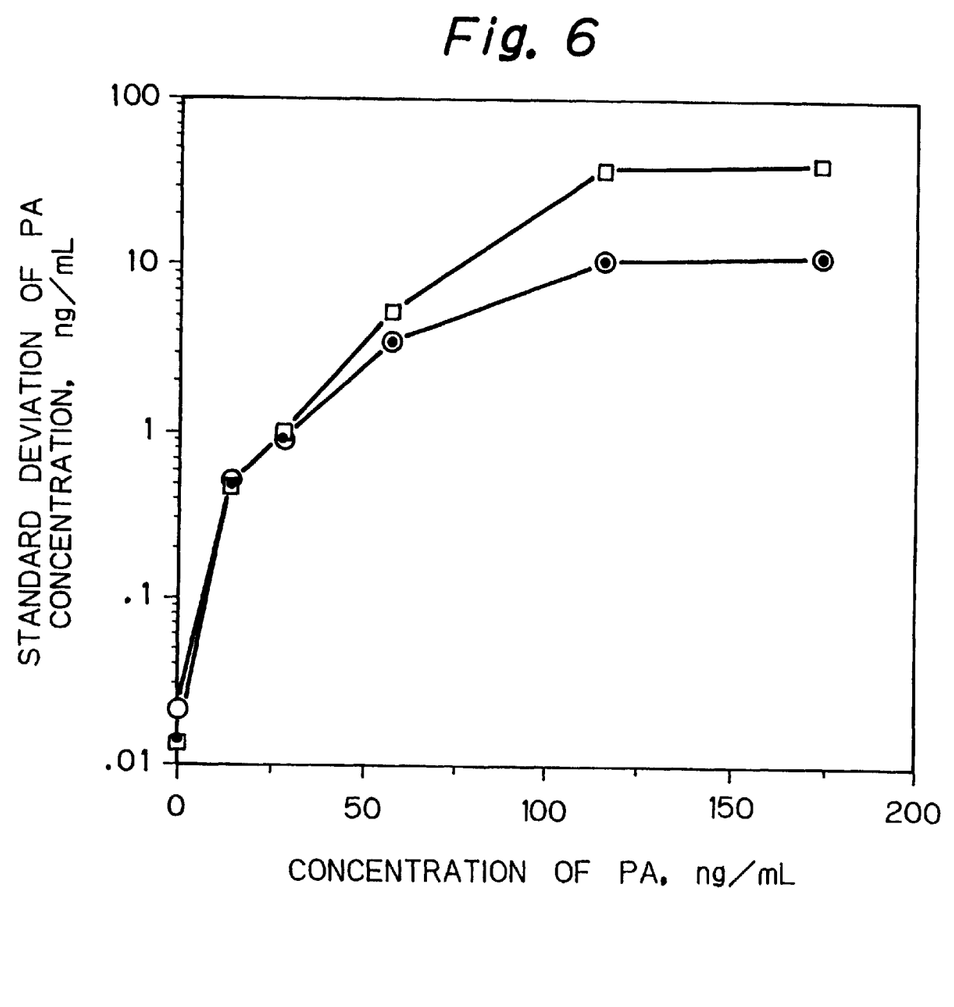
FIG. 6 is a graph showing the standard deviations of PA concentration on PA calibration curves for three cases of weighting four measured values, with the relationship between the point of time and the value of measurement being approximated by a quadratic function, the first case (○) being such that tx which was the rate determining point of time was equated by $tx1=(t1+t2+t3)/3$, the second case (□) being such that tx was equated by $tx2=(t1+t2+t3+t4)/4$, and the third case (●) being such that tx was equated by $tx3=(t1+t2+t3+t4\times w4)/(3+w4)$.

FIG. 6 compares the standard deviations for various PA concentrations between the three cases of rate calculation at points of time tx1, tx2 and tx3. Obviously, the standard deviations for PA concentration at point of time tx3 were close to those at point of time tx2 in the range of lower PA concentrations but close to those at point of time tx1 in the range of higher PA concentrations. This means that be shifting the rate determining point of time in a manner dependent on the weight of a specific measured value in accordance with the method of the invention, one can derive a calibration curve of high linearity that is generally small in fluctuation. By improving the linearity of the calibration curve, the effect of rate decrease which would be caused by the decreasing substrate concentration or the increasing concentration of the decomposition product of the substrate can be compensated; to this end, the rate determined at point of time tx3 was corrected by the following calculation formula: corrected rate=(the rate determined at tx3)×(1+α×(4 MU concentration at tx3)). In the example under discussion, an experimentally given value, namely, 7×10$^{-6}$ was used as α; alternatively, this value may be determined on the basis of the following two relations, one representing the relationship between the reaction rate of ALP in the reaction vessel used and the concentration of 4 MUP and which is determined by a Lineweaver-Bulk plot and the other representing the relationship between the concentration of phosphoric acid which increases upon the decomposition of the substrate 4 MUP and the rate of increase in the reaction product.

Figure 7:
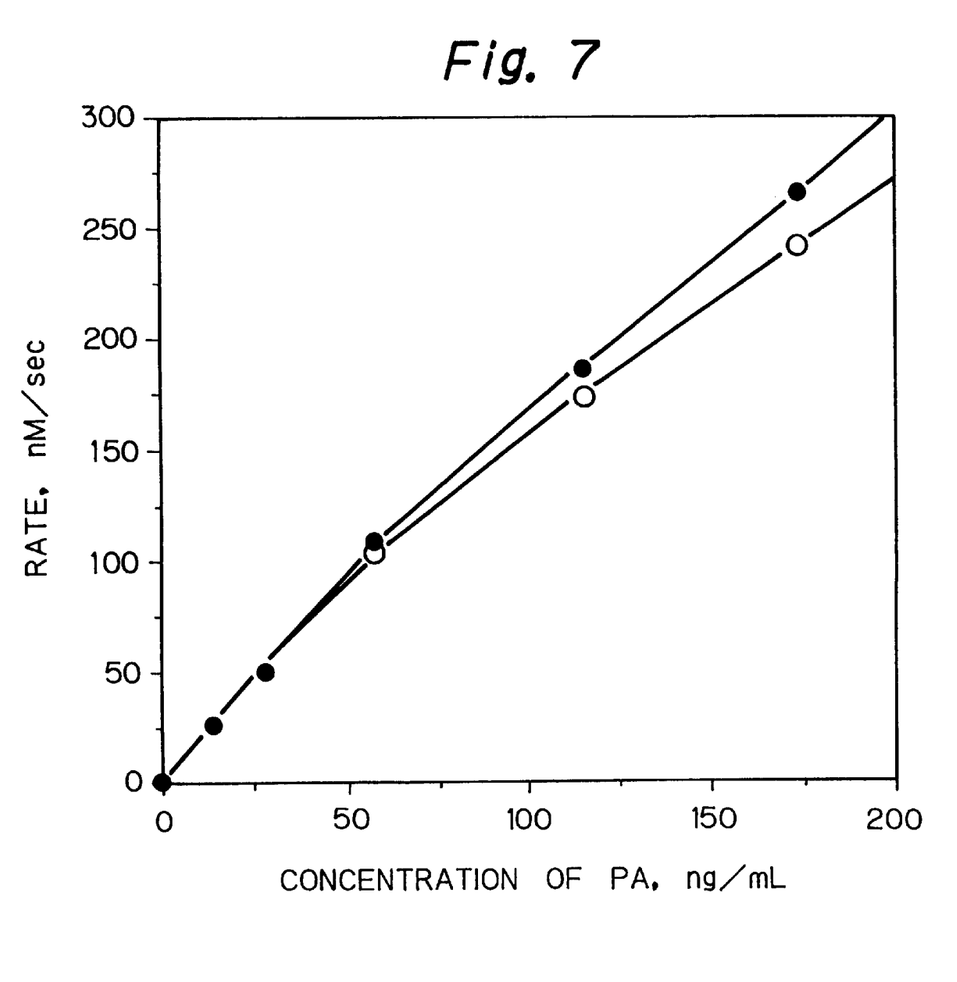
FIG. 7 is a graph comparing two PA calibration curves, one (○) being constructed with the rate determining point of time tx was equated by $tx=(t1+t2+t3+t4\times w4)/(3+w4)$ and the other (●) being constructed after appropriate rate correction.

FIG. 7 shows the PA calibration curves for the case where the rate determining point of time was tx3, one derived when no correction of the kind just described above was effected and the other being derived by performing the correction. The resulting improvement in linearity was particularly noticeable in the region of higher PA concentrations. In fact, the rate correction resulted in simultaneous compensation for the variation in measured values, so the variation in the PA concentration will not change; yet, the linearity of the calibration curve can be improved to provide an improvement in the accuracy of quantified values.

As will be apparent from the foregoing explanation, the present invention can achieve the following advantages in the measurement of enzyme activity and in the method of quantitating substances utilizing the measurement of enzyme activity: (1) even with a limited number of measured values that are obtained by measurement at a limited number of points of time, quantification can be accomplished with high accuracy while maintaining the continuity of a calibration curve; (2) even with measured values that fall within such a concentration range and/or a time range that the rate of enzymatic reaction will drop during the reaction of interest, the continuity of the calibration curve is maintained and yet the accuracy of measurement (quantification) can be improved; and (3) by correcting the determined rate, the linearity of the calibration curve can be enhanced while, at the same time, the inaccuracy of the measurement (quantification) can be reduced to a minimum.

What is claimed is:

1. A method of calculating the rate of increase in the reaction product of an enzymatic reaction, said method comprising the steps of:

(a) measuring at different points of time a signal correlated to the concentration of the reaction product resulting from the enzymatic reaction;

(b) approximating the obtained values measured in step (a) by a specified function of time of measurement; and (c) determining the rate of increase in said reaction product from said function, wherein the approximation of step (b) comprises (1) excluding the obtained measuring values which exceed a preset upper limit in accordance with the detection limit of a detector used in step (a), (2) selecting the measured values obtained at different points of time which measured values are at least equal in number to the independent parameters of the approximating function which selected values are not greater than said upper limit, and (3) weighting the measured values selected in step (2) with a finite value to effect approximation by said function, provided that said finite value for weighting at least a portion of the measured values is changed continuously in accordance with the magnitudes of a portion of the measured values.

2. The method of rate calculation according to claim 1, wherein the approximating function is expressed as a linear or quadratic equation or a linear fractional equation which has 2, 3 or 4 parameters.

3. The method of rate calculation according to claim 1, wherein the approximating function in step (b) is a nonlinear function and a slope of a tangent line on said function is determined to establish the rate, with the point of time for determining the slope of said tangent line being shifted.

4. A method of calculating the rate of increase in the reaction product of an enzymatic reaction said method comprising the steps of:

(a) measuring at different points of time a signal correlated to the concentration of the reaction product resulting from the enzymatic reaction;

(b) approximating the obtained values measured in step (a) by a nonlinear function of time of measurement; and (c) determining the rate of increase in said reaction product from said function, wherein the approximation of step (b) comprises (1) excluding the obtained measuring values which exceed a preset upper limit in accordance with the detection limit of a detector used in step (a), (2) selecting the measured values obtained at different points of time which measured values are at least equal in number to the independent parameters of the approximating function which selected values are not greater than said upper limit, and (3) weighting the measured values selected in step (2) with a finite value to effect approximation by said function, wherein the rate of increase in step (c) comprises determining the slope of a tangent line on said function by shifting the time point for determining the slope of said tangent line to establish the rate.

5. The method of rate calculation according to claim 4, wherein the approximating function is expressed which has 3 or 4 parameters.

6. The method of rate calculation according to claim 1 or 4, wherein the approximating function of step (b) is a nonlinear function, a slope of a tangent line on said function is determined to establish the rate, with the point of time for determining the slope of said tangent line being equal to an average of respective points of time for measurement as calculated on the basis of the weights of the values measured at said respective points of time which are used in approximation by said function.

7. The method of rate calculation according to claim 1 or 4, wherein the approximating function of step (b) is a nonlinear function, and a slope of said function is determined in terms of the slope of a tangent line on said function to establish the rate, with the point of time for determining the slope of said tangent line being shifted in accordance with a provisional rate calculated using at least two of the weighted measured values and the points of time at which they were measured.

8. The method of rate calculation according to any one of claims 1, 2, 4, 5, or 3, wherein the rate from the slope of a tangent line on the approximating function is determined using a corrected rate derived by correcting in accordance with the value of measurement at the rate determining point of time.

* * * * *